(12) United States Patent
Hahn et al.

(10) Patent No.: US 12,370,234 B2
(45) Date of Patent: Jul. 29, 2025

(54) COMPOSITION COMPRISING P53-ACTIVATING PEPTIDE

(71) Applicant: SUPADELIXIR INC., Chuncheon-si (KR)

(72) Inventors: Jang-Hee Hahn, Chuncheon-si (KR); Min-Seo Kim, Chuncheon-si (KR)

(73) Assignee: SUPADELIXIR INC., Chuncheon-si (KR)

( * ) Notice: Subject to any disclaimer, the term of this patent is extended or adjusted under 35 U.S.C. 154(b) by 591 days.

(21) Appl. No.: 17/757,020

(22) PCT Filed: Dec. 9, 2020

(86) PCT No.: PCT/KR2020/017836
§ 371 (c)(1),
(2) Date: Jun. 8, 2022

(87) PCT Pub. No.: WO2021/118199
PCT Pub. Date: Jun. 17, 2021

(65) Prior Publication Data
US 2023/0021365 A1    Jan. 26, 2023

(30) Foreign Application Priority Data
Dec. 10, 2019   (KR) .................. 10-2019-0163920

(51) Int. Cl.
| | | |
|---|---|---|
| *A61K 38/06* | (2006.01) | |
| *A61K 8/64* | (2006.01) | |
| *A61P 17/08* | (2006.01) | |
| *A61Q 19/00* | (2006.01) | |
| *C07K 5/08* | (2006.01) | |

(52) U.S. Cl.
CPC ............. *A61K 38/06* (2013.01); *A61K 8/64* (2013.01); *A61P 17/08* (2018.01)

(58) Field of Classification Search
CPC .. A61K 38/06; A61K 8/64; C07K 5/08; A61P 17/08; A61Q 19/00; A61Q 19/008
See application file for complete search history.

(56) References Cited

U.S. PATENT DOCUMENTS

| | | | |
|---|---|---|---|
| 6,406,898 B1* | 6/2002 | Sakamoto | C12P 41/005 435/243 |
| 8,530,421 B2* | 9/2013 | Hahn | A61P 17/00 424/134.1 |
| 10,706,955 B2* | 7/2020 | Bremel | G16B 20/00 |
| 2012/0094919 A1 | 4/2012 | Graub et al. | |
| 2023/0023726 A1* | 1/2023 | Hahn | A61P 9/10 |

FOREIGN PATENT DOCUMENTS

| | | |
|---|---|---|
| KR | 10-0681701 B1 | 2/2007 |
| KR | 10-0722675 B1 | 5/2007 |
| KR | 10-2018-0099092 A | 9/2018 |

OTHER PUBLICATIONS

Jul. 22, 2018 (Naver blog. "Lighten Up with Hahn's Peptide No-Sebum Sebum Care Cream [Ultimate Relief Cream]"). https://m.blog.naver.com/girlhat/221324296609.
Banting et al., "The MIC2 Gene Product: Epitope Mapping and Structural Prediction Analysis Define an Integral Membrane Protein", Mol. Immunol. (1989) 26: 181-188.
Guerzoni et al., "CD99 Triggering in Ewing Sarcoma Delivers a Lethal Signal through p53 Pathway Reactivation and Cooperates with Doxorubicin", Clin Cancer Res (2015) 21:146-156.
Melnik, "p53: key conductor of all anti-acne therapies", J Transl Med (2017) 15:195-206.

* cited by examiner

*Primary Examiner* — Julie Ha
(74) *Attorney, Agent, or Firm* — Vorys, Sater, Seymour and Pease LLP; Mih Suhn Koh

(57) ABSTRACT

The present invention provides a cosmetic composition for inhibiting or improving seborrhea and a pharmaceutical composition for preventing, improving or treating seborrhea, each composition comprising a specific peptide as an active ingredient. The peptide remarkably decreases the interaction between p53 and MDM2 and thus remarkably increases the interaction between p53 and RNA Polymerase II (POLII), thereby being able to induce expressions of the cytokines that cause apoptosis of sebocytes.

3 Claims, 3 Drawing Sheets

Specification includes a Sequence Listing.

SEQUENCE LISTING

```
<160> NUMBER OF SEQ ID NOS: 20

<210> SEQ ID NO 1
<211> LENGTH: 3
<212> TYPE: PRT
<213> ORGANISM: Artificial Sequence
```

```
<220> FEATURE:
<223> OTHER INFORMATION: Synthetic peptide

<400> SEQUENCE: 1

Leu Glu Asp
1

<210> SEQ ID NO 2
<211> LENGTH: 3
<212> TYPE: PRT
<213> ORGANISM: Artificial Sequence
<220> FEATURE:
<223> OTHER INFORMATION: Synthetic peptide

<400> SEQUENCE: 2

Leu Ser Asp
1

<210> SEQ ID NO 3
<211> LENGTH: 3
<212> TYPE: PRT
<213> ORGANISM: Artificial Sequence
<220> FEATURE:
<223> OTHER INFORMATION: Synthetic peptide

<400> SEQUENCE: 3

Leu Gly Asp
1

<210> SEQ ID NO 4
<211> LENGTH: 3
<212> TYPE: PRT
<213> ORGANISM: Artificial Sequence
<220> FEATURE:
<223> OTHER INFORMATION: Synthetic peptide

<400> SEQUENCE: 4

Leu Ala Asp
1

<210> SEQ ID NO 5
<211> LENGTH: 3
<212> TYPE: PRT
<213> ORGANISM: Artificial Sequence
<220> FEATURE:
<223> OTHER INFORMATION: Synthetic peptide

<400> SEQUENCE: 5

Leu Gln Asp
1

<210> SEQ ID NO 6
<211> LENGTH: 3
<212> TYPE: PRT
<213> ORGANISM: Artificial Sequence
<220> FEATURE:
<223> OTHER INFORMATION: Synthetic peptide

<400> SEQUENCE: 6

Leu Arg Asp
1

<210> SEQ ID NO 7
<211> LENGTH: 3
<212> TYPE: PRT
<213> ORGANISM: Artificial Sequence
<220> FEATURE:
```

```
<223> OTHER INFORMATION: Synthetic peptide

<400> SEQUENCE: 7

Leu Lys Asp
1

<210> SEQ ID NO 8
<211> LENGTH: 3
<212> TYPE: PRT
<213> ORGANISM: Artificial Sequence
<220> FEATURE:
<223> OTHER INFORMATION: Synthetic peptide

<400> SEQUENCE: 8

Leu Leu Asp
1

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide

<400> SEQUENCE: 9

Leu Tyr Asp
1

<210> SEQ ID NO 10
<211> LENGTH: 3
<212> TYPE: PRT
<213> ORGANISM: Artificial Sequence
<220> FEATURE:
<223> OTHER INFORMATION: Synthetic peptide

<400> SEQUENCE: 10

Leu Asp Asp
1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide

<400> SEQUENCE: 11

Leu Phe Asp
1

<210> SEQ ID NO 12
<211> LENGTH: 3
<212> TYPE: PRT
<213> ORGANISM: Artificial Sequence
<220> FEATURE:
<223> OTHER INFORMATION: Synthetic peptide

<400> SEQUENCE: 12

Leu Asn Asp
1

<210> SEQ ID NO 13
<211> LENGTH: 3
<212> TYPE: PRT
<213> ORGANISM: Artificial Sequence
<220> FEATURE:
<223> OTHER INFORMATION: Synthetic peptide
```

<400> SEQUENCE: 13

Leu Cys Asp
1

<210> SEQ ID NO 14
<211> LENGTH: 3
<212> TYPE: PRT
<213> ORGANISM: Artificial Sequence
<220> FEATURE:
<223> OTHER INFORMATION: Synthetic peptide

<400> SEQUENCE: 14

Leu His Asp
1

<210> SEQ ID NO 15
<211> LENGTH: 3
<212> TYPE: PRT
<213> ORGANISM: Artificial Sequence
<220> FEATURE:
<223> OTHER INFORMATION: Synthetic peptide

<400> SEQUENCE: 15

Leu Ile Asp
1

<210> SEQ ID NO 16
<211> LENGTH: 3
<212> TYPE: PRT
<213> ORGANISM: Artificial Sequence
<220> FEATURE:
<223> OTHER INFORMATION: Synthetic peptide

<400> SEQUENCE: 16

Leu Met Asp
1

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide

<400> SEQUENCE: 17

Leu Pro Asp
1

<210> SEQ ID NO 18
<211> LENGTH: 3
<212> TYPE: PRT
<213> ORGANISM: Artificial Sequence
<220> FEATURE:
<223> OTHER INFORMATION: Synthetic peptide

<400> SEQUENCE: 18

Leu Thr Asp
1

<210> SEQ ID NO 19
<211> LENGTH: 3
<212> TYPE: PRT
<213> ORGANISM: Artificial Sequence
<220> FEATURE:
<223> OTHER INFORMATION: Synthetic peptide

```
<400> SEQUENCE: 19

Leu Trp Asp
1

<210> SEQ ID NO 20
<211> LENGTH: 3
<212> TYPE: PRT
<213> ORGANISM: Artificial Sequence
<220> FEATURE:
<223> OTHER INFORMATION: Synthetic peptide

<400> SEQUENCE: 20

Leu Val Asp
1
```

COMPOSITION COMPRISING P53-ACTIVATING PEPTIDE

TECHNICAL FIELD

The present invention relates to a composition comprising a peptide that activates p53. More specifically, the present invention relates to a cosmetic composition for inhibiting or improving seborrhea; and a pharmaceutical composition for preventing, improving or treating seborrhea, each composition comprising a peptide having an activity to remarkably decrease the interaction between p53 and MDM2 and thus to remarkably increase the interaction between p53 and RNA Polymerase II (POLII), as an active ingredient.

BACKGROUND ART

Sebum secreted by sebocytes of the sebaceous gland has advantageous functions, such as preventing the penetration of harmful substances outside the skin and regulating oil and moisture in the skin. However, when sebum is excessively secreted due to changes in puberty hormones, stress, etc., it causes dysfunction and various skin disorders. Seborrhea, which is a disease or skin trouble of the sebaceous gland characterized by excessive secretion of sebum, causes oily coating, crusts or scales, and the like on the skin.

Inhibition or improvement of seborrhea is mainly achieved by hygienic methods such as personal soap washing and shampoo use. As a drug therapy, there are used antifungal agents such as selenium sulfide, azole compounds, sodium sulfacetamide, terbinafine and anti-inflammatory agents such as steroids. However, such a therapy is only for symptom relief and cannot provide fundamental inhibition, improvement, or treatment against seborrhea. Therefore, there is a need in the art to develop a method capable of providing fundamental inhibition, improvement, or treatment against seborrhea.

CD99 is a type 1 transmembrane protein consisting of a glycosylated extracellular region, a transmembrane region and a short intracellular region (Banting, G. S., Pym, B., Darling, S. M., and Goodfellow P. N. (1989). The MIC2 gene product: epitope mapping and structural prediction analysis define an integral membrane protein. Mol. Immunol. 26: 181). It has been reported that, when an anti-CD99 monoclonal antibody is bound with the CD99 molecules expressed in Ewing sarcoma (EWS) cells, MDM2 (which is a E3 ubiquitin ligase) is lost and thus the binding of MDM2 and p53 is inhibited (Guerzoni C. et. al. (2015). CD99 triggering in Ewing sarcoma delivers a lethal signal through p53 pathway reactivation and cooperates with doxorubicin. Clin Cancer Res 21:146-156). The p53 released from MDM2 activates the RNA polymerase complex including RNA Polymerase II (POLII) in the cell nucleus to increase the expression of downstream target genes such as TRAIL (tumor-necrosis factor-related apoptosis-inducing ligand) that causes apoptosis of sebocytes (Melnik B. C. (2017). p53: key conductor of all anti-acne therapies. J Transl Med 15:195-206). In addition, p53 inhibits the IGF-1 signaling and the c-Myc function that induce proliferation and differentiation of sebocytes.

Therefore, It is expected that inhibition of the binding between MDM2 and p53 and increase of the interaction between p53 and POLII make it possible to fundamentally inhibit, improve, or treat seborrhea through inhibiting the proliferation and differentiation of sebocytes and inducing apoptosis of sebocytes.

DISCLOSURE

Technical Problem

The present inventors have found that a certain peptide remarkably increases the interaction between PKA (protein tyrosine kinase) and SHP2 (Src homology region 2 domain-containing phosphatase-2), thereby being able to inhibit cancer cell metastasis mediated by β1 integrin signaling and to be usefully applied for preventing or treating inflammatory diseases (Korean Patent Publication No. 10-2018-0099092). Surprisingly, the present inventors have found that said peptide remarkably decreases the interaction between p53 and MDM2 and thus remarkably increases the interaction between p53 and POLII, thereby exhibiting an activity inhibiting, improving, or treating seborrhea.

Therefore, it is an object of the present invention to provide a cosmetic composition for inhibiting or improving seborrhea, comprising the specific peptide as an active ingredient.

It is another object of the present invention to provide a pharmaceutical composition for preventing, improving or treating seborrhea, comprising the specific peptide as an active ingredient.

Technical Solution

In accordance with an aspect of the present invention, there is provided a cosmetic composition for inhibiting or improving seborrhea, comprising a peptide consisting of three amino acids of the following Formula 1 as an active ingredient:

Leu-X-Asp  <Formula 1> wherein,

X is glutamic acid (Glu), serine (Ser), glycine (Gly), alanine (Ala), glutamine (Gln), arginine (Arg), lysine (Lys), leucine (Leu), tyrosine (Tyr), aspartic acid (Asp), phenylalanine (Phe), asparagine (Asn), cysteine (Cys), histidine (His), isoleucine (Ile), methionine (Met), proline (Pro), threonine (Thr), tryptophan (Trp), or valine (Val), and is a peptide bond.

In accordance with another aspect of the present invention, there is provided a pharmaceutical composition for preventing, improving or treating seborrhea, comprising a peptide consisting of three amino acids of the Formula 1 as an active ingredient.

In the cosmetic composition and the pharmaceutical composition according to the present invention, preferably the peptide may be a peptide consisting of the amino acid sequence of SEQ ID NO: 2, 3, 4, 6, 7, 9 or 18.

Advantageous Effects

It has been found by the present invention that the peptide of Formula 1, i.e., the peptide consisting of three amino acids of Formula 1 remarkably decreases the interaction between p53 and MDM2 and thus remarkably increases the interaction between p53 and POLII. Therefore, since the peptide induces expressions of the cytokines that cause apoptosis of sebocytes, e.g., TRAIL (tumor-necrosis factor-related apoptosis-inducing ligand), it can be usefully applied to a cosmetic composition for inhibiting or improving seborrhea and a pharmaceutical composition for preventing, improving or treating seborrhea.

BEST MODE

Figure 1:
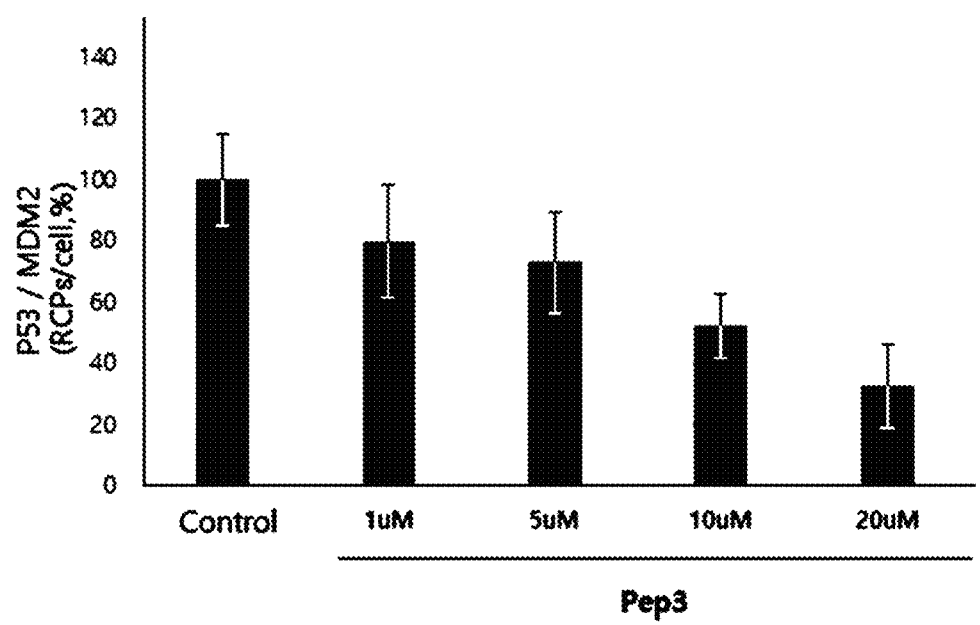
FIG. 1 shows the changes in interaction between p53 and MDM2 according to the treating-concentrations, when human keratinocytes (HaCaTs) were treated with the peptide of the present invention.

As used herein, the term "seborrhea" refers to a disease or skin trouble of the sebaceous gland characterized by excessive secretion of sebum, including acne derived from oversecretion of sebum.

The present invention provides a cosmetic composition for inhibiting or improving seborrhea, comprising a peptide consisting of three amino acids of the following Formula 1 as an active ingredient:

Leu-X-Asp            <Formula 1> wherein,
X is glutamic acid (Glu), serine (Ser), glycine (Gly), alanine (Ala), glutamine (Gln), arginine (Arg), lysine (Lys), leucine (Leu), tyrosine (Tyr), aspartic acid (Asp), phenylalanine (Phe), asparagine (Asn), cysteine (Cys), histidine (His), isoleucine (Ile), methionine (Met), proline (Pro), threonine (Thr), tryptophan (Trp), or valine (Val), and
is a peptide bond.

In addition, the present invention provides a pharmaceutical composition for preventing, improving or treating seborrhea, comprising a peptide consisting of three amino acids of the Formula 1 as an active ingredient.

In the cosmetic composition and the pharmaceutical composition according to the present invention, the peptide consisting of the amino acid sequence of SEQ ID NO: 2, 3, 4, 6, 7, 9 or 18 has been found to have a particularly excellent activity in decreasing the interaction between p53 and MDM2 and thus increasing the interaction between p53 and POLII. Accordingly, in an embodiment, the peptide may be a peptide consisting of the amino acid sequence of SEQ ID NO: 2, 3, 4, 6, 7, 9 or 18.

The cosmetic composition according to the present invention may be prepared, for example, in the form of a functional cosmetic composition. The cosmetic composition may be prepared in various forms according to conventional methods in the field of cosmetic composition. For example, the cosmetic composition may be prepared in forms of cosmetic products, cosmetic solutions, creams, lotions, etc., which may be diluted with a cleansing water, an astringent solution, or a moisture solution, for the use thereof. And, the cosmetic composition may include conventional excipients, such as a stabilizer, a solubilizing agent, vitamins, a pigment, a flavoring agent, which are conventionally used in the field of cosmetic composition. In the cosmetic composition, the peptide may be present in an amount effective to achieve the effect of inhibiting or improving seborrhea, for example, in an amount ranging from about 0.00001 to 1% by weight, preferably in an amount ranging from about 0.001 to 0.1% by weight, based on the total weight of the composition.

The pharmaceutical composition of the present invention may include a pharmaceutically acceptable carrier, for example additives such as lactose or corn starch, lubricants such as magnesium stearate, currently available emulsifiers, suspending agents, buffers, isotonic agents, etc. The pharmaceutical composition of the present invention can be formulated to an oral dosage form or a parenteral dosage form, preferably to a parenteral dosage form for transdermal administration, subcutaneous administration, intramuscular administration, etc. If necessary, excipients such as buffers and isotonic agents may be used for parenteral dosage forms. The pharmaceutical composition may be in the form of an aqueous solution containing a carrier such as phosphate buffered saline (PBS). The pharmaceutical composition of the present invention may be administered to a patient in an amount suitable for preventing, improving, or treating seborrhea, e.g., at a daily dosage of about 0.01 to 10 mg/kg, which may be generally changed according to the age, body weight, and conditions of a patient.

Hereinafter, the present invention will be described more specifically by the following examples and experimental examples. However, the following examples and experimental examples are provided only for illustrations and thus the present invention is not limited to or by them.

Example 1: Synthesis of Peptides

The peptides of SEQ ID NOs: 1 to 20 (see Table 1 below) were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and identified using a mass spectrometer (HP 1100 Series LC/MSD, Hewlett-Packard, Roseville, U.S.A.).

TABLE 1

| Peptide name | SEQ ID NO | Amino acid sequence |
|---|---|---|
| Pep1 | SEQ ID NO: 1 | Leu-Glu-Asp |
| Pep2 | SEQ ID NO: 2 | Leu-Ser-Asp |
| Pep3 | SEQ ID NO: 3 | Leu-Gly-Asp |
| Pep4 | SEQ ID NO: 4 | Leu-Ala-Asp |
| Pep5 | SEQ ID NO: 5 | Leu-Gln-Asp |
| Pep6 | SEQ ID NO: 6 | Leu-Arg-Asp |
| Pep7 | SEQ ID NO: 7 | Leu-Lys-Asp |
| Pep8 | SEQ ID NO: 8 | Leu-Leu-Asp |
| Pep9 | SEQ ID NO: 9 | Leu-Tyr-Asp |
| Pep10 | SEQ ID NO: 10 | Leu-Asp-Asp |
| Pep11 | SEQ ID NO: 11 | Leu-Phe-Asp |
| Pep12 | SEQ ID NO: 12 | Leu-Asn-Asp |
| Pep13 | SEQ ID NO: 13 | Leu-Cys-Asp |
| Pep14 | SEQ ID NO: 14 | Leu-His-Asp |
| Pep15 | SEQ ID NO: 15 | Leu-Ile-Asp |
| Pep16 | SEQ ID NO: 16 | Leu-Met-Asp |
| Pep17 | SEQ ID NO: 17 | Leu-Pro-Asp |
| Pep18 | SEQ ID NO: 18 | Leu-Thr-Asp |
| Pep19 | SEQ ID NO: 19 | Leu-Trp-Asp |
| Pep20 | SEQ ID NO: 20 | Leu-Val-Asp |

Example 2: Preparation of the Compositions Containing Peptides

The peptides of SEQ ID NOs: 1 to 20 were respectively dissolved in phosphate buffered saline (PBS) to a concen-

Experimental Example 1: Evaluation of the Effects of Peptide on the Physical Binding Between p53 and MDM2

After treating cells with the peptide of the present invention, the effects thereof on the physical binding between p53 and MDM2 were evaluated through an in situ PLA (proximity ligation assay) method. HaCaT cells (human keratinocytes, CLS) were added at $4.5 \times 10^4$ cells per well, along with a DMEM containing 10% fetal bovine serum, to each well of a 24-well microplate and then cultured at 37° C. in a 5% $CO_2$ incubator for 24 hours. The peptide solution of Example 2 was added thereto so that the concentration of the peptide in the medium was 1, 5, 10, or 20 μM, followed by incubating for 30 minutes under the same condition. The control group did not receive any treatment. The cells of each well were washed with PBS, fixed by treating with 2% formaldehyde for 15 minutes, and then treated with 0.1% TritonX-100 for 5 minutes to increase antibody permeability into the cells. Anti-p53 polyclonal antibody (Abcam, UK) and anti-MDM2 polyclonal antibody (Santa Cruz, CA, USA) were added thereto. After the PLA probe was added thereto using the in situ PLA kit (Sigma-Aldrich), hybridization, ligation, amplification and mounting steps were carried out according to the manufacturer's protocol. Each physical interaction between p53 and MDM2 was quantified by measuring the luminescence signals (PLA signals) detected in each cell with a confocal laser microscope (Olympus fluoview FW1000; Olympus, Tokyo, Japan). The results thereof are shown in FIG. 1.

From the results of FIG. 1, it can be confirmed that the groups treated with the peptide of the present invention significantly reduced the interaction between p53 and MDM, in comparison with the untreated control group.

Experimental Example 2: Evaluation of the Activities of Peptide on p53 Phosphorylation and MDM2 Loss Phosphorylation of p53 and expression of MDM2 were evaluated using a Western blotting method. The peptide solution of Example 2 was added to the well having HaCaT cells at $5 \times 10^6$ cells per well so that the concentration of the peptide in the medium was 20 μM, followed by incubating for 15 minutes, 30 minutes, or 60 minutes under the same condition. The cells of each well were washed 3 times with PBS and then lysed with a 1% NP40 lysis buffer (1% Nonidet P40, 0.1M NaCl, 0.05M tris (pH 8.0), 5 mM EDTA) containing 0.1 μM PMSP (phenylmethylsulfonyl fluoride), 1 μg/ml pepstatin A, 10 μg/ml leupeptin, 1 μg/ml aprotinin and 1 mM $Na_3VO_4$. After quantifying the cell lysate using the Bradford assay method, the samples for electrophoresis were prepared. The immunoprecipitates were subject to electrophoresis on a 10% polyacrylamide gel. The developed proteins were transferred to a nitrocellulose membrane and then treated with a blocking solution (i.e., a Tris-buffered saline (TBS) containing 0.05% Tween 20 and 3% bovine serum albumin) at room temperature for about 1 hour. Thereafter, the reaction was performed in a TBS (containing 0.5% bovine serum albumin) having anti-p53 polyclonal antibody (Santa Cruz, CA, USA) or anti-MDM2 polyclonal antibody (Santa Cruz, CA, USA) for 2 hours, followed by washing with a TBS containing 0.05% Tween 20. After treatment with horseradish peroxidase conjugated anti-rabbit IgG (Santa Cruz, CA, USA) at room temperature for 1 hour, it was washed 5 times with a TBS containing 0.05% Tween 20 and developed using the antibody detection kit (Ab frontier, Korea). In order to confirm that the same amount of cell lysate was electrophoresed, actin was recognized using an anti-beta actin monoclonal antibody (Santa Cruz, CA, USA). The results thereof are shown in FIG. 2.

Figure 2:
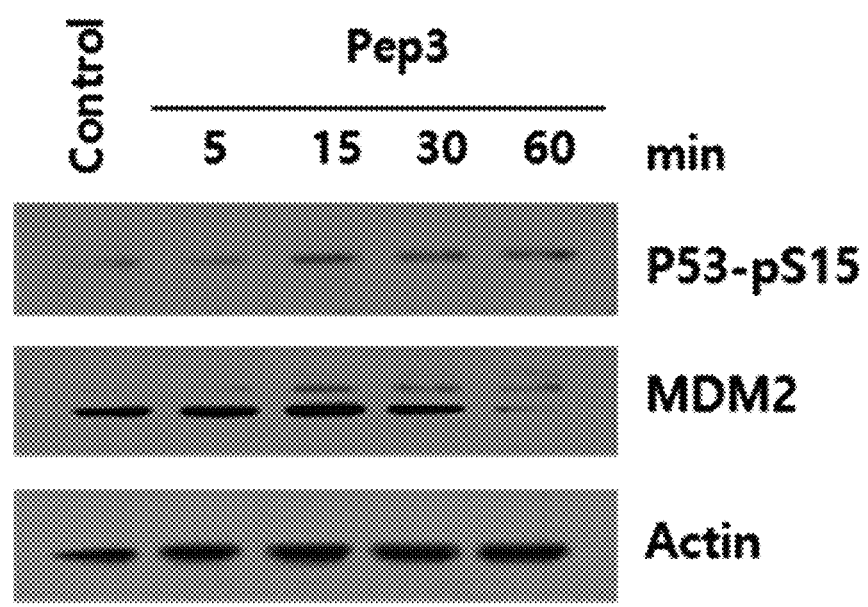
FIG. 2 shows the changes in p53 phosphorylation and MDM2 expression level according to the treating-times, when human keratinocytes (HaCaTs) were treated with the peptide of the present invention.

As can be seen from the results of FIG. 2, the highest increase of p53 phosphorylation was observed at the time of 15 minutes after the peptide treatment; and the MDM2 expression was lost at the time of 60 minutes after the peptide treatment.

Experimental Example 3: Evaluation of the Effects of Peptides on the Physical Binding Between p53 and RNA Polymerase II (POLII)

After treating cells with the peptides of the present invention, the effects thereof on the physical binding between p53 and RNA Polymerase II (POLII) were evaluated through an in situ PLA (proximity ligation assay) method. HaCaT cells (human keratinocytes, CLS) were added at $4.5 \times 10^4$ cells per well, along with a DMEM containing 10% fetal bovine serum, to each well of a 24-well microplate and then cultured at 37° C. in a 5% $CO_2$ incubator for 24 hours. The peptide solutions of Example 2 were added thereto so that the concentration of each peptide in the medium was 20 μM, followed by incubating for 1 hour under the same condition. The control group did not receive any treatment. The cells of each well were washed with PBS, fixed by treating with 2% formaldehyde for 15 minutes, and then treated with 0.1% TritonX-100 for 5 minutes to increase antibody permeability into the cells. Anti-p53 polyclonal antibody (Abcam, UK) and anti-POLII polyclonal antibody (Santa Cruz, CA, USA) were added thereto. After the PLA probe was added thereto using the in situ PLA kit (Sigma-Aldrich), hybridization, ligation, amplification and mounting steps were carried out according to the manufacturer's protocol. Each physical interaction between p53 and POLII was quantified by measuring the luminescence signals (PLA signals) detected in each cell with a confocal laser microscope (Olympus fluoview FW1000; Olympus, Tokyo, Japan). The results thereof are shown in FIG. 3.

Figure 3:
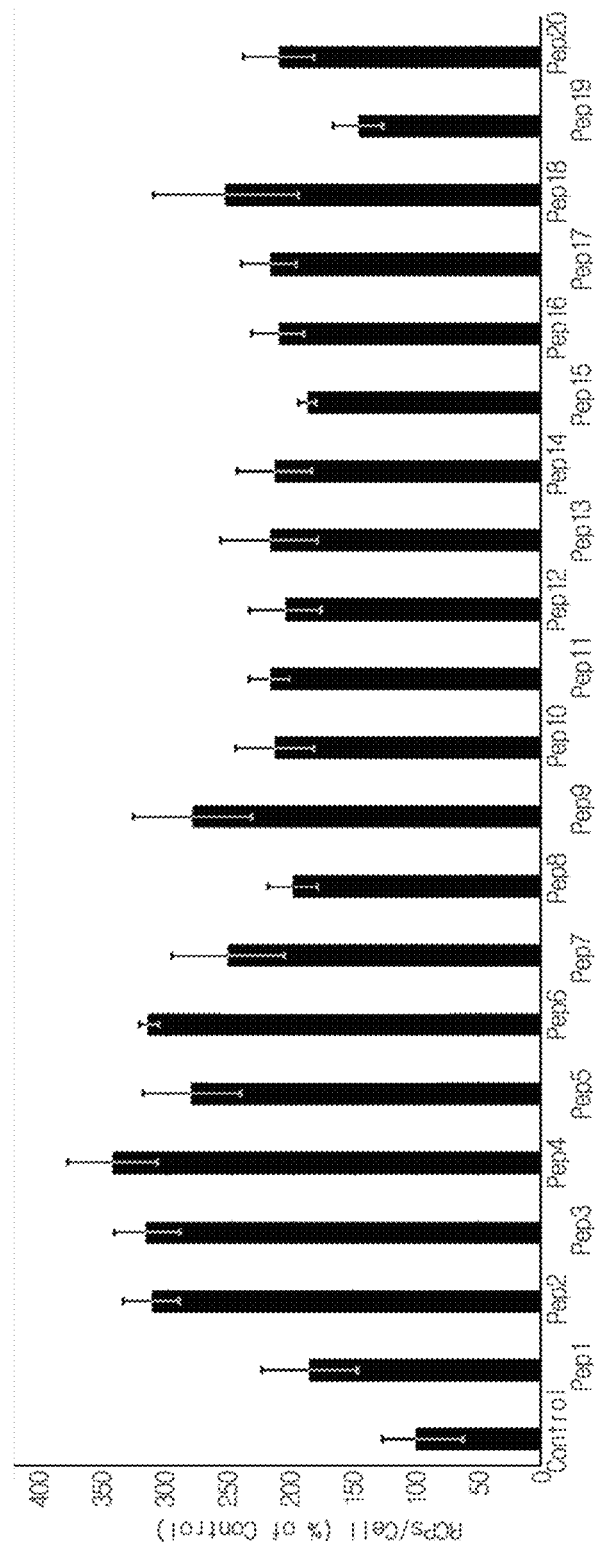
FIG. 3 shows the results obtained by evaluating the effects on the interaction between p53 and POLII, when human keratinocytes (HaCaTs) were treated with the peptides of the present invention.

From the results of FIG. 3, it can be confirmed that the groups treated with the peptides of the present invention significantly increased the interaction between p53 and POLII, in comparison with the untreated control group. In particular, it can be confirmed that Pep 2, 3, 4, 6, 7, 9 and 18 (i.e., the peptides of SEQ ID NOs: 2, 3, 4, 6, 7, 9 and 18) showed remarkably high increases (by more than 2.5-fold) in the interaction between p53 and POLII, in comparison with the control group.

---

The invention claimed is:

1. A method for inhibiting, improving or treating seborrhea, comprising administering to a subject in need thereof a composition comprising an effective amount of a peptide consisting of three amino acids of Formula 1 as an active ingredient:

Leu-X-Asp                    <Formula 1> wherein:

X is selected from the group consisting of glutamic acid (Glu), serine (Ser), glycine (Gly), alanine (Ala), glutamine (Gln), arginine (Arg), lysine (Lys), leucine (Leu), tyrosine (Tyr), aspartic acid (Asp), phenylalanine (Phe), asparagine (Asn), cysteine (Cys), histidine (His), isoleucine (Ile), methionine (Met), proline (Pro), threonine (Thr), tryptophan (Trp), and valine (Val), and is a peptide bond.

2. The method according to claim 1, wherein the peptide is a peptide consisting of the amino acid sequence of SEQ ID NO: 2, 3, 4, 6, 7, 9 or 18.

3. The method of claim 1, wherein the composition is a cosmetic composition comprising a cosmetically acceptable excipient, or a pharmaceutical composition further comprising a pharmaceutically acceptable carrier.

* * * * *